United States Patent
Kessler et al.

(10) Patent No.: US 7,662,147 B2
(45) Date of Patent: Feb. 16, 2010

(54) BEAM STEERING SYSTEM FOR CORNEAL LASER SURGERY

(75) Inventors: Ralf Kessler, Heidelberg (DE); Frieder Loesel, Mannheim (DE); Thomas Sauter, Heidelberg (DE)

(73) Assignee: Technolas PerfectVision GmbH, Munich (DE)

( * ) Notice: Subject to any disclaimer, the term of this patent is extended or adjusted under 35 U.S.C. 154(b) by 202 days.

(21) Appl. No.: 12/028,687

(22) Filed: Feb. 8, 2008

(65) Prior Publication Data

US 2008/0147051 A1     Jun. 19, 2008

Related U.S. Application Data

(62) Division of application No. 10/821,402, filed on Apr. 9, 2004.

(51) Int. Cl.
*A61F 9/008* (2006.01)

(52) U.S. Cl. .................. 606/4; 606/5; 606/18; 372/24; 128/898

(58) Field of Classification Search ................. 606/4–6, 606/10–13, 17; 359/201–202, 209–210; 128/898; 219/121.67–121.68, 121.73–121.8; 372/15–24
See application file for complete search history.

(56) References Cited

U.S. PATENT DOCUMENTS

| | | | | |
|---|---|---|---|---|
| 4,090,781 A | * | 5/1978 | Godot et al. ............. 359/226.1 |
| 4,099,880 A | * | 7/1978 | Kano ......................... 356/611 |
| 4,174,154 A | * | 11/1979 | Kawasaki .................... 359/861 |
| 4,725,709 A | * | 2/1988 | Mattelin ................... 219/121.8 |
| 4,849,859 A | * | 7/1989 | Nagasawa .................... 362/573 |
| 4,901,718 A | * | 2/1990 | Bille et al. ..................... 606/4 |
| 5,200,857 A | * | 4/1993 | Matsushita .................. 359/634 |
| 5,206,763 A | * | 4/1993 | Macken et al. .............. 359/858 |
| 5,411,502 A | * | 5/1995 | Zair ............................. 606/10 |
| 6,074,382 A | * | 6/2000 | Asah et al. ...................... 606/9 |
| 6,165,170 A | * | 12/2000 | Wynne et al. ................... 606/9 |
| 6,210,401 B1 | * | 4/2001 | Lai .............................. 606/12 |
| 6,547,397 B1 | * | 4/2003 | Kaufman et al. .............. 353/28 |
| 6,666,857 B2 | * | 12/2003 | Smith ........................... 606/12 |
| 6,849,824 B2 | * | 2/2005 | Arai et al. ................. 219/121.7 |
| 2002/0153361 A1 | * | 10/2002 | Sakamoto et al. ........ 219/121.73 |
| 2003/0021307 A1 | * | 1/2003 | Yamazaki ..................... 372/24 |
| 2004/0262275 A1 | * | 12/2004 | Kuroiwa et al. ......... 219/121.77 |
| 2005/0283058 A1 | * | 12/2005 | Choo-Smith et al. ......... 600/315 |
| 2007/0020785 A1 | * | 1/2007 | Bruland et al. ................ 438/16 |

\* cited by examiner

*Primary Examiner*—Henry M Johnson, III
*Assistant Examiner*—Aisha Hunte
(74) *Attorney, Agent, or Firm*—Nydegger & Associates

(57) ABSTRACT

A device and method for steering a laser beam to a focal point in target tissue requires generating a laser beam. Diversions of the laser beam from a central beam path are minimized by a sequential arrangement of optical steering components. In order, the beam is first directed to the center of a z-scanning apparatus which will move the focal point in the medium in a z-direction. The beam is then passed to the center of a first galvanometric mirror which introduces focal point movements in the x-direction. A second galvanometric mirror then compensates for the x-direction movement by redirecting the beam to the center of a third galvanometric mirror where focal point movements in the y-direction are introduced.

7 Claims, 2 Drawing Sheets

BEAM STEERING SYSTEM FOR CORNEAL LASER SURGERY

This application is a divisional of application Ser. No. 10/821,402, filed Apr. 9, 2004, which is currently pending. The contents of application Ser. No. 10/821,402 are incorporated herein by reference.

FIELD OF THE INVENTION

The present invention pertains generally to systems and methods for performing corneal laser surgery. More particularly, the present invention pertains to systems and methods for optically steering a laser beam to perform corneal laser surgery. The present invention is particularly, but not exclusively useful as a system for optically steering a laser beam to a focal point in a medium, while maintaining the beam path substantially centered on the optical components of the system, for corneal laser surgery.

BACKGROUND OF THE INVENTION

Corneal laser surgery requires moving and focusing (i.e. steering) a laser beam to a succession of many predetermined focal points. Depending on the particular surgical procedure that is to be performed, these predetermined focal points may be either on or within a medium (target tissue). In either case, the intended purpose is to photoalter target tissue in accordance with a predetermined pattern. In refractive surgery, for example, the target tissue is normally stromal tissue in the cornea of a human eye, and the steering of the laser beam is accomplished by the moving, tilting or realigning of optical components (i.e. lenses and mirrors) of the laser system.

Laser surgery systems that are currently being used typically include a dual-mirror combination that is manipulated to move and direct the laser beam as the beam transits the system. Within this combination, one mirror is moved to effect movements of the laser beam's focal point in an x-direction on an x-y plane in the target tissue. The other mirror is then moved to effect movements of the focal point in a y-direction on the x-y plane in the target tissue. The result here is that for each of these movements, the laser beam will necessarily be directed away from a central path through the system. Moreover, these effects are cumulative. Thus, it will happen that as the laser beam is moved to effectuate "x" and "y" movements for a particular laser surgical pattern, the center of the beam path will be moved away from the center of downstream optical components in the system. At some point, the combined effects of these movements can significantly reduce the optical efficiency and the surgical precision of the laser system.

In light of the above, it is an object of the present invention to provide a device for steering a laser beam to a focal point in a medium during laser surgery wherein movements of the laser beam are compensated to maintain the beam substantially centered on the optical components of the system as the beam transits the system. Yet another object of the present invention is to provide a device for steering a laser beam to a focal point in a medium during corneal laser surgery wherein displacements of the laser beam, from the center of optical elements, are minimized during "x", "y" and "z" movements of the laser beam's focal point in a target tissue. Still another object of the present invention is to provide a device for steering a laser beam to a focal point in a medium during corneal laser surgery that is easy to use, relatively simple to manufacture, and comparatively cost effective.

SUMMARY OF THE INVENTION

In accordance with the present invention, a device for steering a laser beam along a beam path to a focal point in a medium includes a laser source for generating the laser beam along a beam path. Additionally, first, second and third scanning mechanisms are positioned sequentially along the beam path for steering the laser beam. The combined effect of these three scanning mechanisms is to produce movements of the focal point on an x-y plane, in the medium (target tissue). In the preferred embodiment of the present invention, the first, second and third scanning mechanisms are galvanometric mirrors. In addition to the three scanning mechanisms, the device of the present invention also includes a z-scanning apparatus for moving the focal point of the laser beam in a z-direction that is perpendicular to the x-y plane. In one embodiment of the present invention, the apparatus is a voice coil subassembly. In an alternate embodiment, the apparatus is an active mirror.

As intended for the present invention, diversions or displacements of the laser beam from the centers of optical components in the system are minimized by the proper placement of optical components along the beam path, and by the incorporation of a third scanning mechanism. In particular, the z-scanning apparatus is placed first in line, after the laser source, and is positioned to receive the laser beam at the center of the apparatus. The z-scanning apparatus then causes the laser beam to converge or diverge to effect a z-movement of the beam's focal plane. The z-scanning apparatus then passes the beam directly toward the center of the first galvanometric mirror. Optically, the first galvanometric mirror is positioned on the beam path to effect a change in an x-direction on the x-y plane whenever the first galvanometric mirror is rotated through an angle of "$\theta$". Next, the second galvanometric mirror is positioned on the beam path to compensate for any beam path diversion that is introduced by the first galvanometric mirror. Specifically, this is done by rotating the second galvanometric mirror through an angle of "$2\theta$", to redirect the beam path onto the center of the third galvanometric mirror. The third mirror can then be rotated through an angle "$\phi$" to effect a change in the y-direction on the x-y plane.

Structurally, the respective axes of rotation for the first, second and third galvanometric mirrors are all perpendicular to the beam path. Further, the axes of rotation of the first and second galvanometric mirrors are parallel to each other. The axis of rotation for the third galvanometric mirror, however, is perpendicular to the axes of rotation of both the first and the second galvanometric mirrors. It is also important within the combination of galvanometric mirrors that the center-to-center distance between the first and second mirrors be equal to the center-to-center distance between the second and third mirrors. As disclosed by the present invention, the "center-to-center" distance is defined as the distance between the geometric centers of the reflective surfaces of any two mirrors optically aligned in the beam path.

Preferably, the device also includes a computer controller that is connected in electronic communication with the z-scanning apparatus and with each of the three galvanometric mirrors. With these connections, the computer controller concertedly controls the functioning of the z-scanning apparatus, and the rotation of the mirrors. Accordingly, the computer controller is capable of controlling movements of the laser beam focal point in an x-y-z volume of target tissue in the medium during laser surgery. Furthermore, the computer controller can be programmed to account for the optical properties of the optical components (e.g. field curvature of a lens), as well as the optical properties of the scanned medium (e.g. index of refraction).

After the laser beam has passed through the optical components disclosed above, it is important that the laser beam be incident substantially near the center of a focusing lens, before the beam enters the medium. To assist in accomplishing this, the device includes relay optics that are positioned on the beam path, downstream from the steering optics. Also, in a preferred embodiment of the present invention, a dichroic turning mirror can be located between the relay and the focusing lens, for directing the laser beam toward the focusing lens. Additionally, a microscope can be cited through the dichroic turning mirror and aligned with the laser beam for viewing the eye of the patient during the laser surgery procedure.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
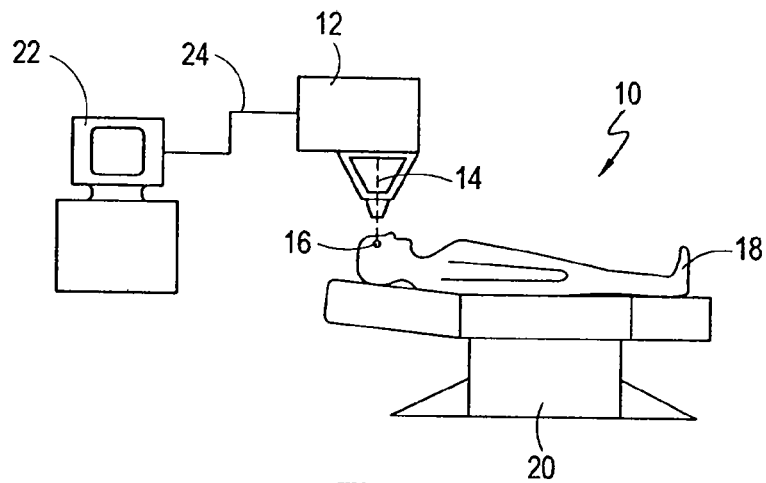
FIG. 1 is an elevational view of a system incorporating the present invention for performing corneal laser surgery.

A system for performing corneal laser surgery is shown in FIG. 1 and is generally designated 10. As shown, the system 10 includes a surgical laser unit 12 for directing a laser beam 14 along a beam path toward an eye 16 of a patient 18. Additionally, the system 10 includes a platform 20 for aligning the eye 16 of the patient 18 with the surgical laser unit 12. Further, a computer controller 22 is in electronic communication with the surgical laser unit 12 via an electrical cable 24, for monitoring and controlling the laser surgery procedure.

Figure 2:
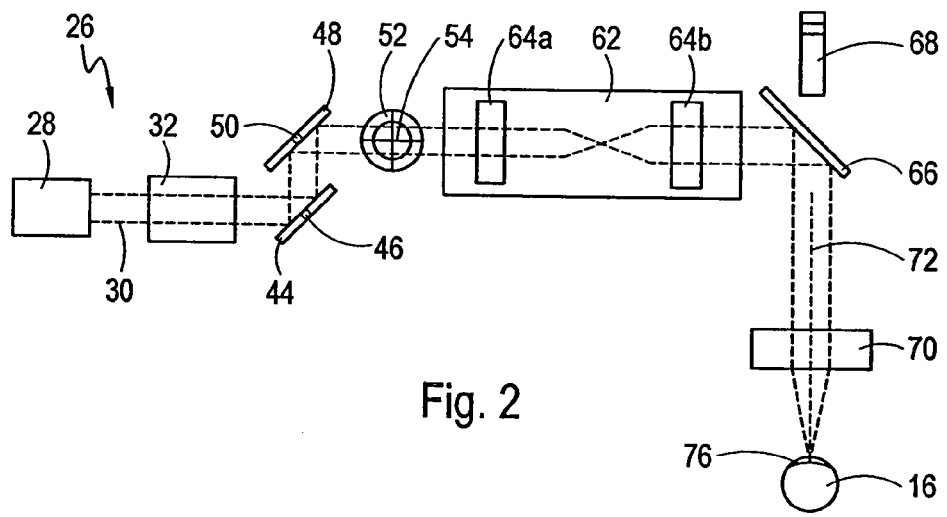
FIG. 2 is a schematic view of the optical components of a device, in accordance with the present invention, for steering a laser beam to a focal point in a medium.

Referring now to FIG. 2, an optical device for steering the laser beam 14 to a focal point in a medium, in accordance with the present invention, is shown and is generally designated 26. Generally, the device 26 will be an integral part of the surgical laser unit 12. In any event, as shown, the device 26 includes a laser source 28 for generating and directing the laser beam 14 along a beam path 30 toward the eye 16. Preferably, the laser source 28 is a femtosecond laser source 28, which is to say a laser source that generates a laser beam 14 having a wavelength of about one micron, a pulse duration in the range of about 100-1000 femtoseconds, and a pulse energy in the range of 0.1 to 100 mJ.

Figure 3A:
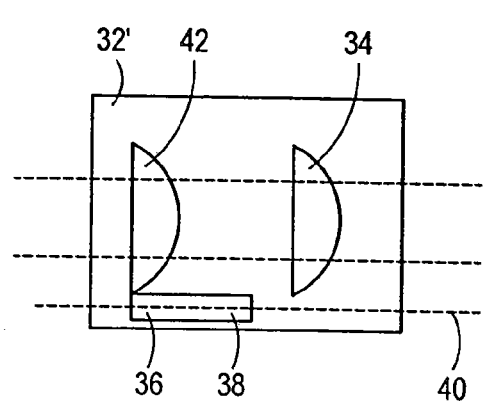
FIG. 3A is a schematic view of one embodiment of the z-scanning apparatus of the present invention, specifically a voice coil subassembly.
Figure 3B:
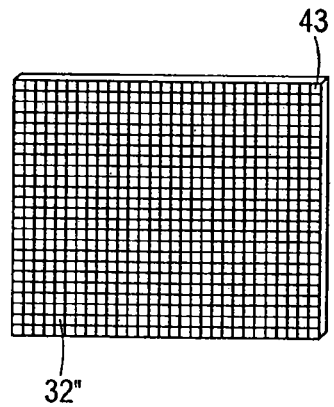
FIG. 3B is a representative illustration of an alternate embodiment of the z-scanning mechanism of the present invention, specifically an active mirror.

As shown in FIG. 2, the device 26 of the present invention includes a z-scanning apparatus 32 that is positioned on the beam path 30 for moving the focal point in a z-direction. Referring for a moment to FIGS. 3A and 3B, two alternate embodiments of the z-scanning apparatus 32 are shown. In FIG. 3A, a voice coil subassembly 32' includes a lens 34 fixedly positioned on the beam path 30. Preferably, the lens 34 is a plano-convex lens. Additionally, the subassembly 32' includes a voice coil 36 having a movable, linear slide 38 that defines a longitudinal axis 40. As shown, the longitudinal axis 40 is parallel to the beam path 30. Further, a lens 42, which is preferably a plano-concave lens, is mounted on the linear slide 38 for movement therewith back and forth along the beam path 30. As shown in FIG. 3B, an alternate embodiment of the z-scanning apparatus 32 is an active mirror 32". More specifically, the mirror 32" may be of the type disclosed in U.S. Pat. No. 6,220,707, entitled "Method for Programming an Active Mirror to Mimic a Wavefront" issued to J. Bille. As can be appreciated by referring to FIG. 3B, the mirror 32" comprises a plurality of individual facets, of which facet 43 is exemplary. Importantly, the facet 43 may be independently moved to change the shape of the surface of the active mirror 32" to alter the incoming beam 14 of light. It should be appreciated that the location of the z-scanning apparatus 32 on the beam path 30, i.e. after the laser source 28 and upstream from the remaining optical elements of the device 26, allows the beam 14 to pass through the center of the apparatus 32, which is desirable when focusing the beam 14 to a focal point in the eye 16.

Figure 4:
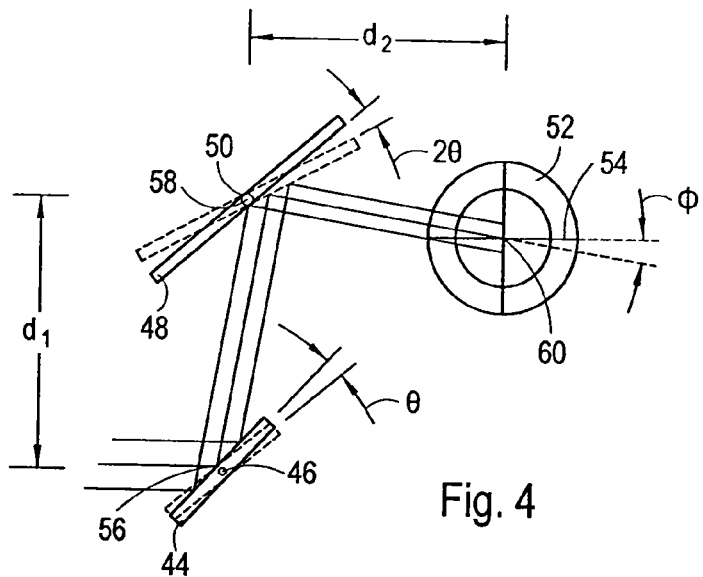
FIG. 4 is a functional layout of galvanometric mirrors for steering a laser beam in accordance with the present invention.

In addition to the z-scanning apparatus 32, the device 26 includes a scanning mechanism 44, which is preferably a galvanometric mirror, positioned on the beam path 30 for rotation of the mirror 44 through an angle "θ". The mirror 44 has an axis of rotation 46 that is perpendicular to the beam path 30. Also positioned on the beam path 30 is a scanning mechanism 48, which is also preferably a galvanometric mirror. As contemplated by the present invention, the mirror 48 has an axis of rotation 50 that is perpendicular to the beam path 30 and parallel to the axis of rotation 46 of the mirror 44. As shown in FIG. 4, the mirror 48 is positioned to rotate through an angle of "2θ". Further, a scanning mechanism 52 is positioned on the beam path 30 to be optically aligned with the mirror 48. In the preferred embodiment of the present invention, the scanning mechanism 52 is a galvanometric mirror, positioned on the beam path 30 for rotation through an angle "ϕ". It can be seen in FIGS. 2 and 4 that the mirror 52 has an axis of rotation 54 that is perpendicular to both the axes of rotation 46 and 50, and that is perpendicular to the beam path 30. Structurally, the distance, "$d_1$" (FIG. 4), between the center 56 of the mirror 44 and the center 58 of the mirror 48, is equal to the distance "$d_2$" between the center 58 and the center 60 of the mirror 52.

Continuing along the beam path 30, it can be seen in FIG. 2 that the device 26 includes a relay 62 positioned downstream from both the z-scanning apparatus 32 and from the mirrors 44, 48 and 52. As shown, the relay 62 comprises a plurality of lenses of which lenses 64a and 64b, are exemplary. In addition to the relay 62, a dichroic turning mirror 66 is positioned for directing the laser beam 14 toward the eye 16 as the beam 14 exits the relay 62. More specifically, the turning mirror 66 is positioned sequentially on the beam path 30 after the relay 62, and the mirror 66 is oriented at substantially a 45° angle relative to the beam path 30. In addition to the dichroic mirror 66, the device 26 of the present invention includes a microscope 68 optically aligned with the dichroic turning mirror 66 and the beam path 30, for viewing the eye 16 of the patient 18 during the laser surgery procedure.

Still referring to FIG. 2, the device 26 also includes a focusing lens 70 positioned on the beam path 30 for focusing the laser beam 14 to the focal point in the eye 16. More specifically, the focusing lens 70 is positioned downstream from the turning mirror 66. As shown in FIG. 2, the focusing lens 70 is a lens multiplet. Further, as envisioned by the present invention, the focusing lens 70 defines a central axis 72. It can be appreciated that the relay 62 is located upstream from the focusing lens 70 for optically imaging the galvanometric mirror 52 onto the surface of the focusing lens 70. Stated differently, the net effect of the beam 14 passing through the relay 62, prior to transiting the focusing lens 70, is that the galvanometric mirror 52 and the focusing lens 70 are optically conjugated.

Figure 5:
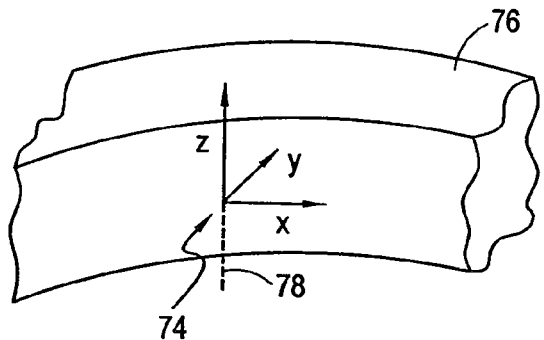
FIG. 5 is a perspective view of section of a medium (target tissue) that defines an orthogonal coordinate system.
Figure 6:
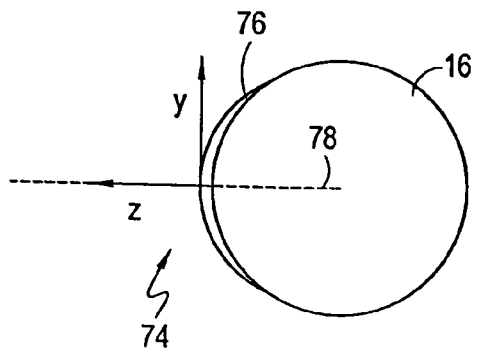
FIG. 6 is a cross-sectional view of a human eye.

In the operation of the present invention, the laser source 28 generates a laser beam 14 that is directed toward the eye 16. More specifically, the laser beam 14 is steered to a focal point within a particular layer, or medium, of the eye 16. As contemplated by the present invention, the medium defines an orthogonal x-y-z coordinate system, of which the coordinate system 74 in FIGS. 5 and 6 is exemplary. As can be seen by cross-referencing FIGS. 5 and 6, the medium is the cornea 76 of the eye 16, and the x-y plane of the coordinate system 74 is normal to the optical axis 78 of the eye 16. As further shown in FIGS. 5 and 6, the z-axis of the coordinate system 74 is substantially coincident with optical axis 78.

Considering still further the operation of the present invention, the laser beam 14 exits the laser source 28 and travels along the beam path 30 towards the z-scanning apparatus 32. In one embodiment of the present invention (FIG. 3A), the computer controller 22 directs the linear slide 38 of the voice coil subassembly 32' to move axially along the longitudinal axis 40 a specified distance. Consequently, the lens 42, which is mounted on the linear slide 38, moves axially as well. Functionally, the movement of the focusing lens 42 relative to the stationary lens 34 causes the beam 14 to diverge or converge, depending on the direction of movement of the lens 42. As a result of the divergence or convergence of the beam 14, the x-y plane of the coordinate system is effectively moved along the z-axis to focus the focal point on the plane. It should be appreciated that the divergence and convergence of the beam 14 may also be accomplished by other means known in the pertinent art, such as by the use of an active mirror 32". More particularly, prior to the laser beam 14 reaching the active mirror 32", the computer controller 22 directs the movement of the individual facets, e.g. 43, of the mirror 32" to focus the focal point along the z-axis.

After exiting the z-scanning apparatus 32, the laser beam 14 continues along the beam path 30 toward the first galvanometric mirror 44. As can be seen by cross-referencing FIGS. 2 and 4, the laser beam 14 is directed toward the center of the mirror 44. As shown in FIG. 4, the mirror 44 rotates, as directed by the computer controller 22, about the axis of rotation 46 through an angle of "θ". As the laser beam 14 reflects off the mirror 44, the orientation of the mirror 44 relative to the angle of incidence of the beam 14, produces a corresponding x-direction movement of the focal point in the cornea 76. More specifically, the focal point moves along the x-axis of the x-y plane of the coordinate system 74 through a distance "Δx" that is proportional to the angle of rotation "θ".

In concert with the rotation of the mirror 44, the mirror 48 rotates about the axis of rotation 50 through an angle of "2θ". As the laser beam 14 reflects off the mirror 48, the laser beam 14 is compensated to align the beam path 30 with the center of the mirror 52, while maintaining the "Δx" movement introduced by the rotation of the mirror 44. In this way, the laser beam 14 reflects off the center of the mirror 52, wherein the beam 14 is moved in a y-direction. More particularly, the mirror 52 is directed by the computer controller 22 to rotate about the axis of rotation 54 through an angle "φ". Consequently, rotation of the mirror 52 though an angle "φ" moves the focal point of the beam 14 a linear distance "Δy" along the y-axis of the x-y plane.

Referring once again to FIG. 2, the laser beam 14 reflects off the third mirror 52 and enters the relay 62. In the relay 62, the laser beam 14 transits the lenses 64a and 64b, during which time the beam path 30 is positioned to be centered on the central axis 72 of the focusing lens 70 when the laser beam 14 is incident on the focusing lens 70. More specifically, the laser beam 14 is focused by lenses 64a and 64b to optically position the y-direction mirror 52 coincident with the focusing lens 70. As such, the mirror 52 changes the angle of incidence of the beam 14 prior to the beam 14 striking the focusing lens 70. There is not, however, any lateral movement of the beam 14 away from the center of the focusing lens 70 as the beam 14 reflects off the mirror 52 and transits the relay 62. As the laser beam 14 exits the relay 62 and reflects off the turning mirror 66, the turning mirror 66 directs the beam 14 toward the focusing lens 70. At the focusing lens 70, the laser beam 14 strikes the center section of the lens 70. As the laser beam 14 transits the focusing lens 70, the laser beam 14 is focused onto the desired focal point in the cornea 76 of the eye 16. Throughout the course of the laser surgery procedure, a system operator (not shown) may view the eye 16 of the patient 18 through the microscope 68 which is aligned with the dichroic turning mirror 66.

While the particular Beam Steering System for Corneal Laser Surgery as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for moving the focal point of a laser beam through a medium, which comprises the steps of:

directing the laser beam along a beam path to the center of a z-scanning apparatus wherein the z-scanning apparatus is moveable to change the location of the focal point in the medium in a z-direction;

passing the laser beam from the center of the z-scanning apparatus to the center of a first scanning mechanism, wherein the first scanning mechanism is rotated through an angle "θ" to alter the beam path and introduce a change in the location of the focal point in the medium in an x-direction; and directing the laser beam from the first scanning mechanism to a second scanning mechanism;

rotating the second scanning mechanism through an angle "2θ" to compensate for the altered beam path and directing the laser beam to the center of a third scanning mechanism, wherein the third scanning mechanism is rotated through an angle "φ" to alter the beam path and introduce a change in the location of the focal point in the medium in a y-direction.

2. A method as recited in claim 1 further comprising directing the laser beam from the third scanning mechanism to a focusing lens positioned on the beam path, with said focusing lens defining a central axis, and further wherein the beam path is substantially centered on the central axis of said focusing lens when the laser beam is incident on said focusing lens.

3. A method as recited in claim 1 wherein said laser beam focused on the medium is a femtosecond laser beam having a wavelength of about one micron, a pulse duration in the range of 100-1000 femtoseconds, and a pulse energy in the range of 0.1 to 100 mJ.

4. A method as recited in claim 1 wherein the medium focused on by the laser beam is a cornea of an eye and further wherein the eye has an optical axis and the optical axis of the eye is substantially aligned along the z-axis of the x-y-z coordinate system.

5. A method for establishing a beam path between a laser source and a focal point in a medium, said method comprising the steps of:

positioning a first scanning mechanism to define a first axis of rotation through an angle "$\theta$" for movement of the focal point in a x-direction the medium;

locating a second scanning mechanism to define a second axis of rotation through an angle "$2\theta$" to compensate for the movement of the first scanning mechanism, wherein the second axis is substantially parallel to the first axis and is located at a distance "d" from the first axis;

placing a third scanning mechanism to define a third axis of rotation through an angle "($\phi$)" for movement of the focal point in a y-direction in the medium, wherein the third axis is substantially perpendicular to the second axis and is placed at a distance "d" from the second axis; and directing the laser beam from the laser source along the beam path extending substantially from the laser source to a center point on the first axis of the first scanning mechanism, and from there to the second scanning mechanism for further direction from the second scanning mechanism to a center point on the third axis of the third scanning mechanism, for subsequent incidence of the laser beam at the focal point in the medium.

6. A method as recited in claim 5 wherein the medium defines an orthogonal x-y-z coordinate system and the method further comprises the step of maintaining the focal point in a selected x-y plane in the medium.

7. A method as recited in claim 6 further comprising the step of concertedly rotating the first, second and third mechanisms to orient the laser beam on the beam path for movement of the focal point in the x-y plane.

* * * * *